United States Patent [19]
Sofield

[11] Patent Number: 5,627,367
[45] Date of Patent: May 6, 1997

[54] RADIATION BEAM CALIBRATER

[75] Inventor: Jack C. Sofield, Seymour, Tenn.

[73] Assignee: Sofield Science Services, Inc., Seymour, Tenn.

[21] Appl. No.: 662,313

[22] Filed: Jun. 13, 1996

Related U.S. Application Data

[62] Division of Ser. No. 541,374, Oct. 10, 1995.

[51] Int. Cl.$^6$ ..................................................... G01T 1/29
[52] U.S. Cl. .......................................................... 250/252.1
[58] Field of Search ...................................... 250/252.1 R

[56] References Cited

U.S. PATENT DOCUMENTS

| | | | |
|---|---|---|---|
| 3,569,711 | 3/1971 | Stoms | 250/375 |
| 3,654,468 | 4/1972 | Shah | 250/302 |
| 5,006,714 | 4/1991 | Attix | 250/368 |
| 5,440,135 | 8/1995 | Shonka | 250/374 |
| 5,511,549 | 4/1996 | Legg et al. | 128/653.1 |

OTHER PUBLICATIONS

*Medical Physics Magazine*, Sep. 1995, vol. 22, No. 9 (insert advertisement).

*Primary Examiner*—Constantine Hannaher
*Attorney, Agent, or Firm*—Luedeka, Neely & Graham, P.C.

[57] ABSTRACT

A radiation beam scanner system employs a peak detection methodology to measure the intensity and distribution of radiation produced by a medical linear accelerator. The scanner system combines the capability to perform scanning measurements with the capability to perform high accuracy calibrations of the linear accelerator. The system employs two ion chamber detectors, signal and reference, with the signal detector positioned within a tank of water (phantom tank). As the water is irradiated by the linear accelerator, the signal detector is continuously moved within the water by means of electrical stepper motors as the reference detector remains stationary at some point within the radiation beam. The reference detector output is compared to a predetermined threshold and, when the threshold is reached, a peak detector circuit monitors the signal detector output for a radiation pulse peak. Accelerator anomalies are eliminated by calculating a ratio of the signal detector output to the reference detector output. Each ratio is time tagged and correlated to signal detector position information, thereby providing a map of the distribution and intensity of the radiation within the water. The resultant data is evaluated by a qualified medical physicist to ascertain the accelerator's suitability for use in dosimetry. In one embodiment, the pulse frequency of the accelerator is determined and the rate of signal detector movement (scan rate) is set as a function of the pulse frequency of the accelerator. The system includes a unique, integrating, auto-zeroing, calibration electrometer that can be employed to calibrate the accelerometer.

7 Claims, 13 Drawing Sheets

RADIATION BEAM CALIBRATER

This is a division of application Ser. No. 08/541,374, filed Oct. 10, 1995.

TECHNICAL FIELD

The present invention relates to the field of radiation beam scanning to determine the distribution and intensity of the radiation. More particularly, this invention relates to measurement of the distribution and intensity of radiation produced by medical linear accelerators used for the treatment of malignant neoplasms, and the calibration of such linear accelerators.

BACKGROUND OF THE INVENTION

Medical techniques for the treatment of malignant neoplasms in patients often involve the use of radiation. A radiation source, such as a medical linear accelerator, is typically used to generate and direct radiation onto a target area of the patient's body. When applied in the proper doses (dosimetry), the radiation produces an ionizing effect on the malignant tissue, thereby killing the malignant cells without causing significant detrimental effect to the surrounding healthy tissue.

The operational characteristics and output levels of medical linear accelerators are varied. The most common type of accelerator is one that produces pulsed radiation that is output as a rectangular beam with a cross-sectional area typically ranging between 16 to 1600 square centimeters. Continuous (non-pulsed) medical devices, such as a cobalt machine, are also used as a radiation source for treating malignant neoplasms. Other accelerators exist that utilize a swept electron beam modality. These machines sweep a very narrow electron beam across the treatment field by means of varying electromagnetic fields.

All linear accelerators used for the treatment of malignant neoplasms must be calibrated. By this process, a determination is made of how much radiation, in terms of Greys, is produced for each monitor unit displayed on the machine console. The American Association of Physicists in Medicine (AAPM) has established protocols (TG-21 and TG-25) for the required correlation procedures for both electron and photon radiation. There are currently no known radiation measurement systems capable of producing, as an output, calibration data that is in compliance with AAPM protocols. Instead, the measurement data produced by known systems must first be modified by the proper calibration units in order to perform machine calibrations.

The intensity and duration of the radiation treatment must be carefully calculated and administered to produce optimized therapeutic results with attendant patient safety. If too much radiation is administered, the radiation's curative effects may be overwhelmed by its destructive effects to the tissue surrounding the malignancy. If an insufficient amount of radiation is delivered, a tumorcidal dose may not be achieved. Therefore, it is important to know how much radiation will be produced per monitor unit by a particular machine and how that radiation will be distributed within the patient's body.

To accurately determine the intensity and duration (dosage) of radiation received by the patient, a pattern, or map, of the radiation at varying positions within the patient's body must be produced. These patterns, often referred to as profiles, iso-dose lines or depth dose curves, depending on the type of presentation, are used to model the distribution of radiation inside the patient undergoing the external beam radiation treatment. The resultant data is then evaluated by a qualified medical physicist to ascertain the machine's suitability for use in dosimetry. The data that makes up the pattern is also used by clinical personnel or a treatment planning system computer to determine the machine on time or monitor units required for the prescribed treatment.

Existing systems for measuring radiation produced by medical linear accelerators employ a tank filled with water with a radiation detector immersed within the water. The composition of the human body closely approximates that of water, so the tank (water phantom) provides a good medium for simulating the distribution and intensity of radiation within the patient's body. Radiation produced by the linear accelerator is directed at the water in the phantom tank where the intensity of the radiation at varying depths and positions within the water is measured with the radiation detector. Scattered radiation produced as the primary radiation penetrates the water, as well as direct or primary radiation, is detected by an ion chamber detector, which is essentially an open air capacitor, producing an electrical current corresponding to the number of ions produced within its volume.

A common technique for processing the ion chamber output is to integrate the signal over a fixed period of time. The detector is lowered to a measurement point within the phantom tank where measurements are taken over a time period. The detector is then moved to another measurement point and measurements are taken as the detector is held in position. For each measurement, a statistically significant number of samples is required, so the detector must be held stationary at the measurement position until the required number of readings have been taken. When measuring radiation produced by machines employing an electron swept beam, the detector must remain in position until a sufficient amount of current has been stored.

The signal integration technique typically employs two detectors—a signal channel and a reference channel. This technique chooses a time interval and then presumes that a statistically significant signal will be output by the detector during that time interval. In other words, the signal integration technique does not take into account the fact that the radiation source may be producing pulsed radiation. For a system employing a pulsed radiation source, a statistically significant signal cannot be assured since the measurement period can begin at any time during the pulse train. Moreover, the signal integration technique cannot account for pulses that are dropped to maintain output, as in the case of Varian accelerators with the Dose Rate Servo activated.

Another known technique for processing the ion chamber detector output is a voltage plotting technique. Electrical current output by the detector is converted to a corresponding voltage signal and plotted as a function of the position of the detector within the phantom tank. Each channel must be independently balanced or signal saturation may occur. The resultant data must be further processed by mathematical smoothing techniques before it is considered useable.

Thus, there is a need for a system that can measure the distribution and intensity of radiation produced by medical linear accelerators as the detector is continuously swept through the phantom tank with no mathematical data smoothing required. The system should exhibit the same stability as the accelerator energy output and maintain precise time synchronization with pulsed linear accelerators. Additionally, the system should be capable of providing the necessary functions to calibrate the accelerator based on AAPM Protocol 21 (for photon measurement) and Protocol 25 (for electron measurement).

SUMMARY OF THE INVENTION

In accordance with a preferred embodiment, the present invention discloses a radiation detection system for determining the distribution and intensity of radiation produced by a radiation source, such as a medical linear accelerator. The linear accelerator may be a pulsed or a continuous machine. The system includes a medium, such as water, for receiving radiation from the radiation source. As the medium is being irradiated by the linear accelerator, a radiation signal detector, such as an ion chamber detector, disposed within the medium senses the amount of radiation at a range of sensing positions within the medium. A detector circuit is connected to the signal detector for producing a signal detector output in the form of an electrical current representing the intensity of radiation sensed by the detector at the sensing positions. A peak detector circuit receives and processes the signal detector output and detects the peak amplitude values of the signal detector output, producing a peak detector signal corresponding to the peak amplitude values and the sensing positions. Finally, data storage means are provided for receiving the peak detector signal and storing data corresponding to the peak amplitude values and the sensing positions associated with the peak amplitude values. This stored data constitutes the intensity and distribution of the radiation.

Further provision is made for the addition of a radiation reference detector. A reference detector circuit is connected to the radiation reference detector for producing a reference detector output in the form of an electrical current representing the intensity of the sensed radiation. A reference peak detector circuit receives and processes the reference detector output and detects the peak amplitude values of the reference detector output, producing a reference peak detector signal corresponding to the peak amplitude values of the reference detector signal. Radiation source anomalies are eliminated by determining ratios of the peak detector signal to the reference peak detector signal. These ratios represent the intensity of radiation peaks in the medium. A computer receives the ratios and correlates them to a sensing position.

Peak detection of the radiation may be performed with the signal detector stationary or continuously moving. Therefore, the system may employ means for continuously moving the signal detector within the medium at a scan speed, through a plurality of predetermined travel intervals corresponding to the range of sensing positions. As the signal detector senses radiation, it produces a signal detector output containing one or more peak amplitude values for each predetermined travel interval. These peak amplitude values represent the distribution and intensity of radiation pulse peaks within the medium.

When performing scanning measurements of a pulsed radiation source, the system may include means for determining the pulse frequency of the radiation source. The signal detector scan speed is then adjusted as a function of the radiation source pulse frequency. For example, the signal detector scan speed may be set so that during a predetermined interval of movement, at least one pulse of radiation will be transmitted by the radiation source. In this example, the controller produces at least one peak amplitude value for each predetermined interval of signal detector movement.

Means for averaging the signal/reference detector ratios over a plurality of predetermined intervals may be employed to produce an average ratio over the intervals. When the scan is complete, the data will represent a map, or a distribution of the average radiation intensities over each of the averaged intervals. In one embodiment, each predetermined travel interval equals 0.25 millimeters. In other words, the scan distance of the signal detector is set at 0.25 millimeters, during which travel at least one pulse of radiation produced by the radiation source will be detected.

The peak detector circuit may further include means for comparing the signal detector output to a predetermined threshold. When the threshold is reached, peak monitoring of the signal detector output commences. When the signal detector output falls below the threshold, peak monitoring ceases. The predetermined threshold may be determined as a percentage of the radiation pulse peaks.

Because the peak detection methodology provides highly accurate and stable measurements of the radiation source energy output, the system may further include means for calibrating the radiation source. These means may include an integrating, self-zeroing, calibration electrometer for converting the signal detector output from an electrical current to an electrical charge. The electrical charge produced by the calibration electrometer is stored in a precision capacitor. The coulomb value of the stored charge corresponds to the amount of radiation output by the radiation source.

The system may further include the necessary components for performing percent depth dose (PDD) measurements in accordance with AAPM TG-25 protocol for electron detection. This capability is provided by employing a voltage supply for applying a bias voltage having a polarity across the signal detector. Means are provided for moving the signal detector in directions of descent into and ascent from the medium. As the signal detector transitions from descent into the medium to ascent from the medium, the polarity of the bias voltage is reversed.

A method of determining the intensity and distribution of radiation produced by a radiation source is also disclosed. The method includes the steps of providing a medium for receiving radiation from the radiation source. Radiation produced by the radiation source is sensed with a signal detector at a plurality of sensing positions, producing a signal output in the form of an electrical current representative of the intensity of radiation sensed. The signal detector is moved within the medium at a scan speed while detecting radiation. Peak amplitude values of the signal detector output are detected, and peak signal values representing the intensity and distribution of radiation pulse peaks are produced. Data corresponding to the peak amplitude values and the sensing positions is then stored.

The method may further include the steps of sensing radiation produced by the radiation source with a reference detector at one location, producing a reference detector output in the form of an electrical current representative of the intensity of radiation sensed at the location. Accelerometer anomalies are eliminated from the signal detector output by determining ratios of the peak signal values to corresponding peak reference values. Each of the ratios corresponds to the intensity of radiation at a sensing position. The ratios can then be correlated to one of the sensing positions.

For detecting the peak amplitude values, the method may include the steps determining a threshold value and then comparing the signal output to the threshold value. When the threshold value is reached, the signal detector output is monitored for a pulse peak.

Prior to commencing scanning measurements, the pulse frequency of the radiation source may be determined and used to set the scan speed of the signal detector. The scan speed is then a function of the pulse frequency.

Signal detector movement may further include the step of moving the signal detector a predetermined interval within the medium at a scan speed sufficient to ensure that at least one pulse of radiation will be transmitted by the radiation source during each predetermined interval of signal detector movement, so that at least one peak amplitude value is produced for each predetermined interval of signal detector movement. As a further method step, the peak amplitude values may be averaged over a plurality of predetermined intervals.

The method may further include steps for performing a percent depth dose (PDD) scan for electron detection. To perform a PDD scan, a bias voltage having a bias polarity is applied across the signal detector. The signal detector is moved vertically down into the medium and then reverses direction and ascends from the medium. As the signal detector transitions from descent to ascent, the polarity of the bias voltage is reversed.

Another preferred method disclosed by the present invention is a method of calibrating a radiation source. To perform calibrations, a medium is provided for receiving radiation from the radiation source. Radiation produced by the radiation source is sensed with a radiation detector disposed within the medium, producing a detector output in the form of an electrical current representative of the amount of radiation output by the radiation source. An integrating, self-zeroing, calibration electrometer with automatic temperature and pressure correction is provided to convert the detector output from an electrical current to an electrical charge corresponding to the amount of radiation output by the radiation source. An adjustment value is determined from the electrical charge and the radiation source output is adjusted to one radiation source monitor unit for each unit of radiation output.

BRIEF DESCRIPTION OF THE DRAWINGS

The invention will now be described in further detail with reference to the drawings wherein like reference characters designate like or similar elements throughout the several drawings as follows.

DETAILED DESCRIPTION OF THE PREFERRED EMBODIMENT

Figure 1:
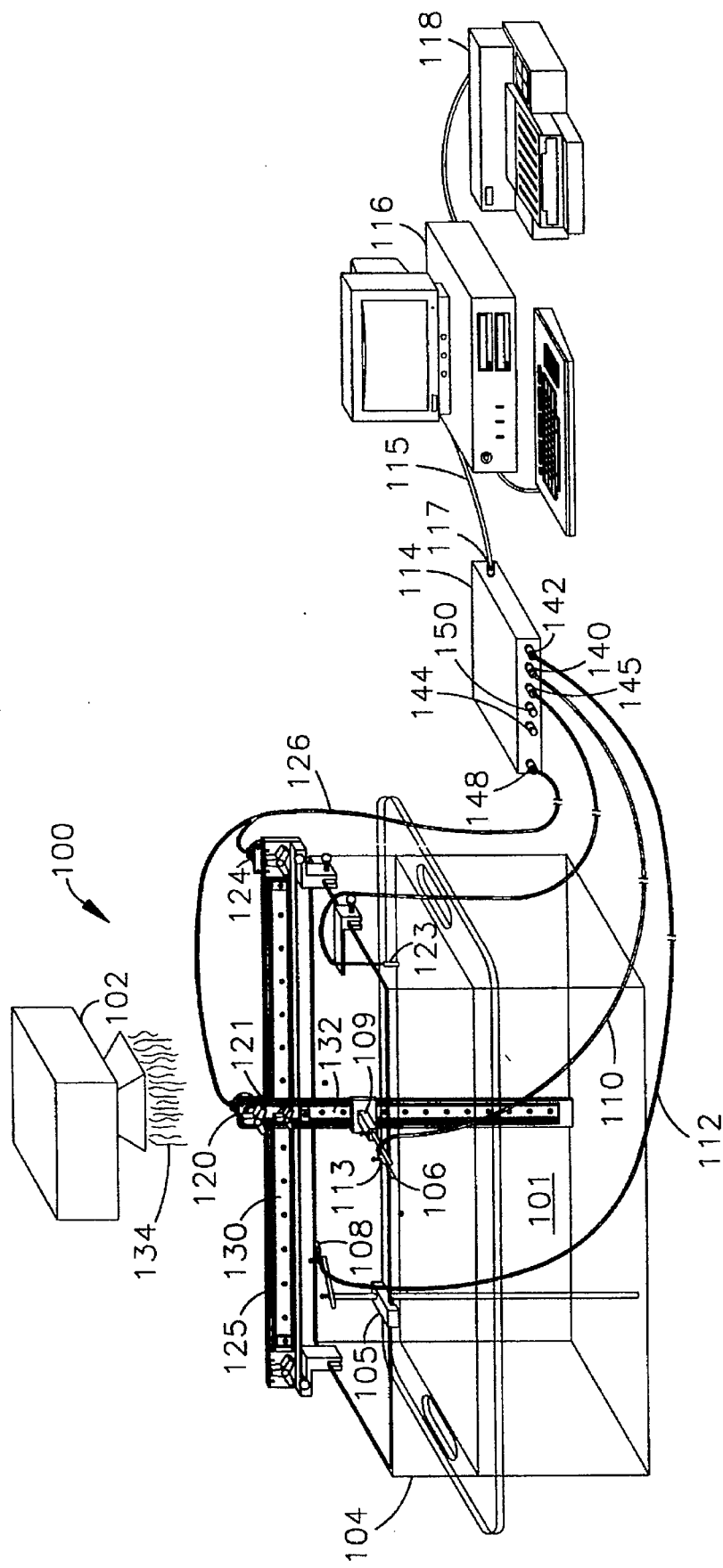
FIG. 1 is an isometric drawing illustrating the overall configuration and setup of the radiation beam scanner system.

In accordance with a preferred embodiment of the present invention, FIG. 1 illustrates a radiation beam scanner system 100 for determining the distribution and intensity of radiation produced by a medical linear accelerator 102 used by medical personnel for the treatment of malignant neoplasms, and for calibrating the medical linear accelerator 102 in accordance with American Association of Physicists in Medicine (AAPM) protocol 21 for photon detection and protocol 25 for electron detection. Scanning data produced by the system 100 is evaluated by a qualified medical physicist to ascertain the accelerator's suitability for use in dosimetry. Calibration data, in the form of coulomb measurement units, is used to calibrate the linear accelerator by adjusting the amount of output per monitor unit.

As shown in FIG. 1, the scanner system 100 includes a water tank 104 (phantom tank) filled with water 101, signal channel detector 106, reference channel detector 108, electronic controller 114, computer 116, and printer 118 (optional). In a preferred embodiment, computer 116 is a notebook computer. To protect the system operator from the hazards of radiation produced by the linear accelerator 102, the controller 114, computer 116, and printer 118 are located in a room that is separate from the room containing the linear accelerator 102 and phantom tank 104. The distance is approximately 50 feet with adequate shielding. When filled with water, the phantom tank 104 simulates body tissue through which radiation produced by the linear accelerator 102 will act upon. Since the density of the human body is approximated by water, the phantom tank provides a good medium for simulating the effects of radiation in the patient. The phantom tank 104 is preferably made of an acrylic or Plexiglas™ material and has dimensions that are compatible with the largest radiation field sizes commonly encountered on linear accelerators. A tank 104 with a length of approximately 68 cm and width of 35 cm has been determined as suitable for most applications. The tank 104, when filled with water, weighs several hundred pounds and requires additional support when placed on the accelerator treatment couch (not shown). In a preferred embodiment, a simple hydraulic jack system with adjustable post (not shown) provides ample support.

Radiation measurements may be performed with the signal detector 106 stationary within the water 101 or moving (scanning). Attached to the phantom tank 104 are a horizontal scanning bar 130 and a vertical scanning bar 132 for moving the signal channel detector 106 through the water 101 during scanning measurements and calibrations. The reference channel detector 108, which is structurally supported in a preferred embodiment as shown and attached to the side of the tank 104 by means of a clamp 105, or clamped to the bottom of the tank (photons only) remains stationary during operation. The reference detector 108 is positioned within the radiation beam 134 at a point above or below the water surface so as not to interfere with the detection of the signal detector 106 as it moves through the water. The signal channel detector 106 is supported by a holder 113, which is attached to the guide block 109 of the vertical scanning bar 132. Stepper motors 124 and 120, which receive electrical excitation from controller 114 via cables 126 and 122 respectively, are attached to horizontal and vertical scanning bars 130, 132 respectively to provide two-dimensional movement of the signal channel detector 106.

In an alternate embodiment, signal detector 106 is replaced with a plurality of detectors geometrically arranged in a one-dimensional detector array, or row, which requires no horizontal movement when the array is properly oriented within the tank 104. Two-dimensional as well as three-dimensional detector arrays may also be employed in place of the discrete signal detector 106 shown in FIG. 1, with the multi-dimensional arrays requiring no movement within the tank 104.

Although stepper motors are used in the preferred embodiment, it will be understood that other motor types, such as servo motors, may be used as well. Stepper motor 124 drives belt 125 which in turn moves horizontal scanning bar 132 in a direction horizontal to the surface of the water 101. Stepper motor 120 drives belt 121 which in turn moves the guide block 109 in a direction vertical to the water surface. An adjustable signal detector holder 113 is used to attach the signal detector 106 at a fixed distance from the vertical scanning bar 132 so that stepper motors 120, 124 cooperate to move the signal detector 106 in a two-dimensional plane through the water 101.

With continued reference to FIG. 1, signal detector 106 and reference detector 108 are preferably ion chamber type detectors. In a preferred embodiment, detectors 106, 108 are 0.3 cm$^3$ (internal volume), PTW waterproof detectors capable of detecting either photons or electrons and providing an output in pico-amps. Although not required for the operability of the system 100, the addition of the reference detector 108 is preferred in order to enhance the stability of the measurements, as will be more fully discussed herein. As a photon or electron passes through an ion chamber detector 106, 108, a small amount of electrical current is produced and output to the controller 114 via a rubber encased, tri-axial cable 110, 112 terminated with a tri-axial connector. Tri-axial cables 110, 112 are preferably low noise cables with an outer shield to reduce microphonic noise generated in the accelerator room. Tri-axial cables have been found to be particularly suitable for supplying the bias required by each of the detectors 106, 108. Each detector 106, 108 communicates with the atmosphere, even when under water, through an attached waterproof sheath. Preferably, the detectors 106, 108 have an outer acrylic cap, an external diameter of 7 mm, and a wall thickness of 0.7 mm. This size and configuration has been found to be particularly suitable for producing an acceptable signal level while maintaining good spatial resolution. Since the response of ion chamber type detectors is a function of ambient air pressure and water temperature, a temperature sensor 123 is immersed in the water 101 and its output provided to the controller 114. For determining ambient air pressure, a pressure sensor 188 (FIG. 3) is positioned within the controller 114.

Figure 2A:
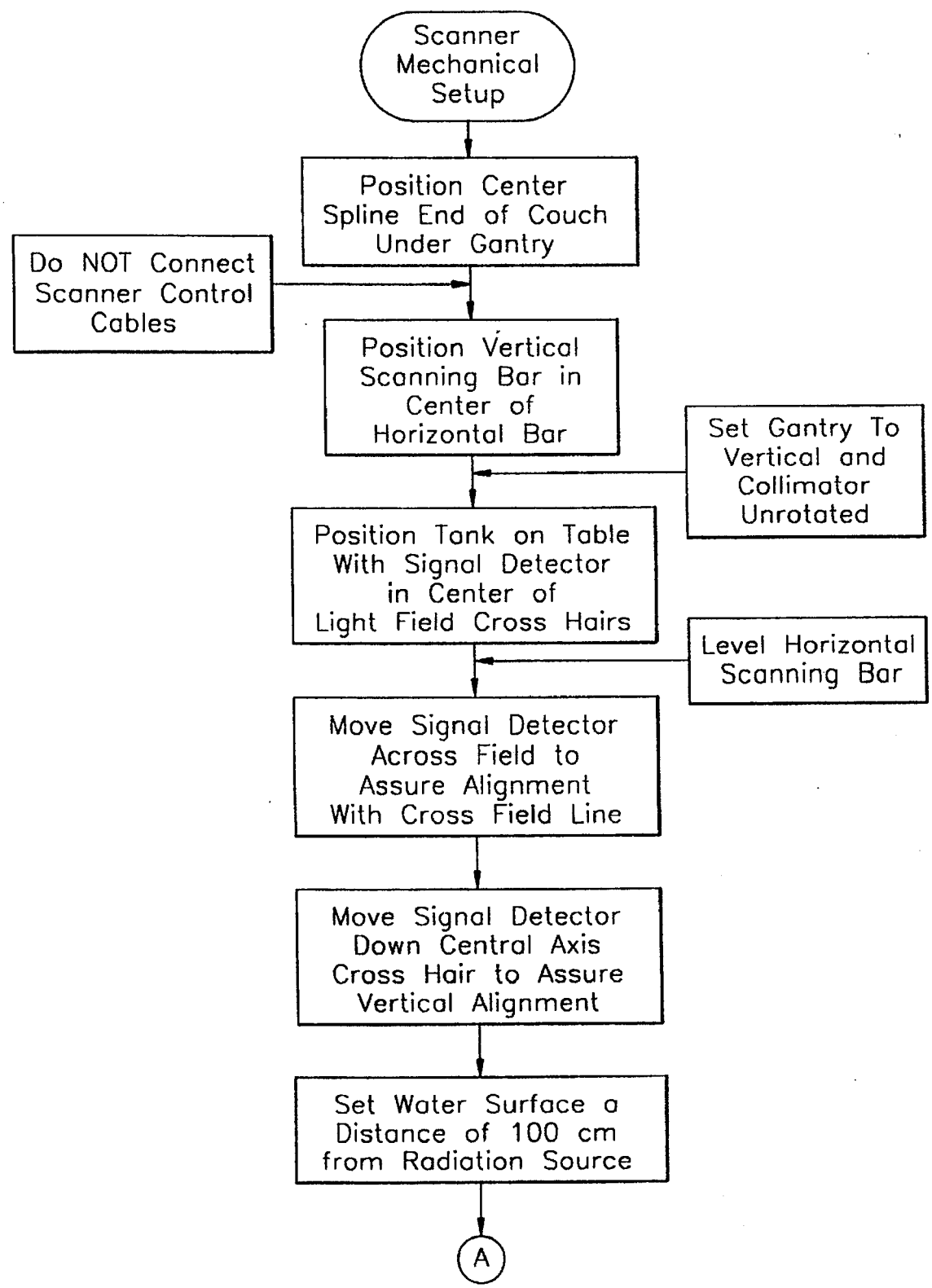
FIGS. 2A and 2B collectively are a flow diagram illustrating the mechanical setup of the scanner system.
Figure 2B:
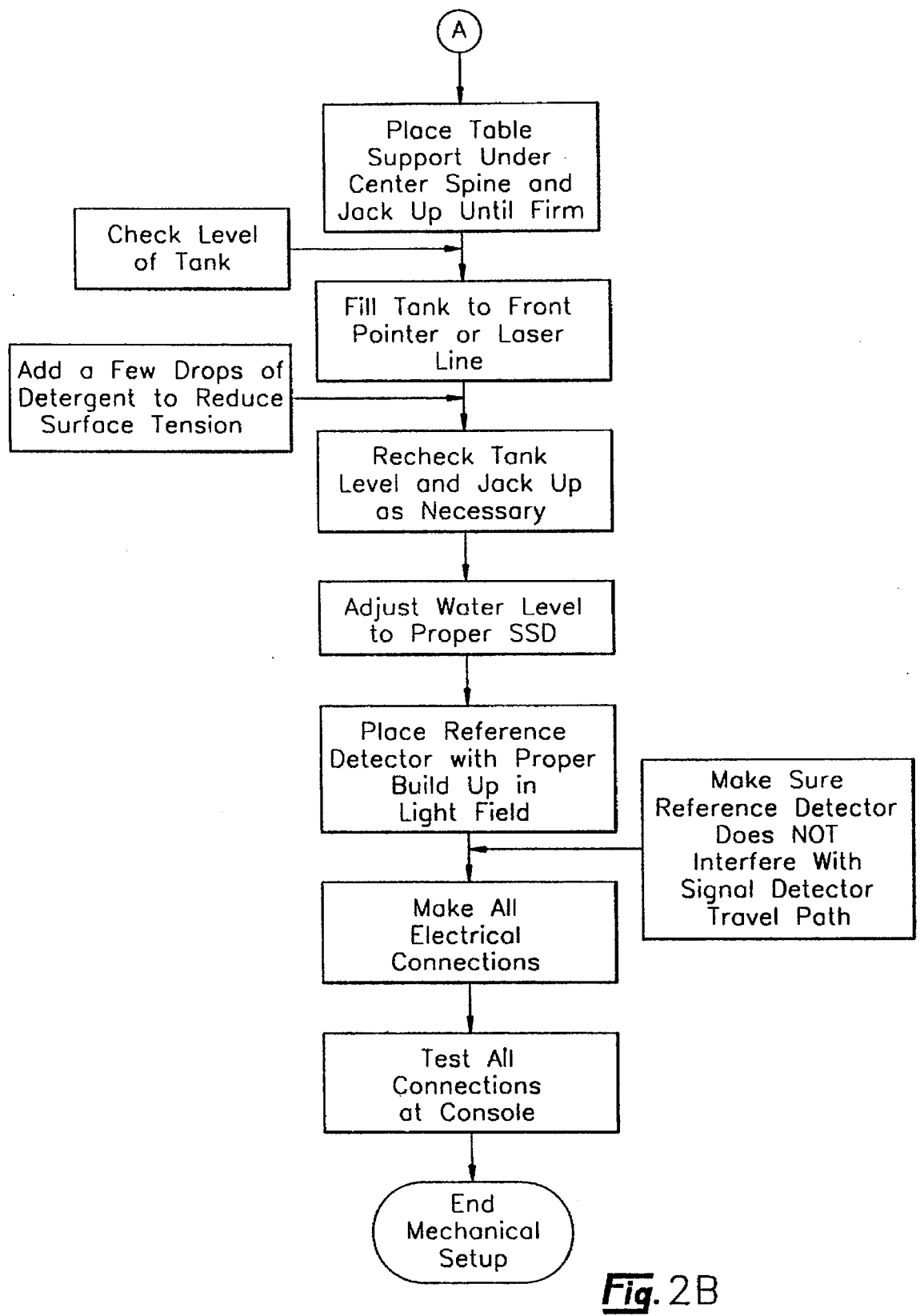

FIGS. 2A and 2B provide a flow diagram illustrating the mechanical setup of the scanner system 100. Although not included within the illustration of FIG. 1, it will be understood that the phantom tank 104 is to be positioned on the patient treatment couch directly beneath the collimator of the linear accelerator 102 with the signal detector 106 initially centered within the radiation beam 134. Due to the weight of the tank 104 when filled with water 101, the tank should be supported and positioned with the aid of a hydraulic jack. Centering the signal detector 106 within the radiation beam 134 is accomplished by positioning the detector 106 within the cross hairs of the accelerator alignment light field. Vertical alignment of the signal detector 106 with the beam 134 is verified by moving the detector 106 up and down while centered within the cross hairs. The reference detector 108 is placed at a point within the light field so as not to interfere with radiation beam impingement on the signal detector 106. Horizontal alignment lasers (not shown), which are typically used for aligning the treatment target area of the patient, may be used during setup to set the height of the phantom tank 104 (e.g., to set the distance of the phantom tank 106 from the linear accelerator radiation source). In a preferred embodiment, the distance from the radiation source to the water surface is 100 cm. As an alternative to the horizontal alignment lasers, most linear accelerators are equipped with a front pointer (not shown) which extends downward from the accelerator head to a distance of 100 cm from the radiation source. This pointer may be used to position the water surface at 100 cm from the radiation source by aligning the lower rod tip end with the water surface. The horizontal and vertical scanning bars 130, 132 should be leveled, and the accelerator should be leveled so that the radiation beam 134 is perpendicular to the water surface.

The detectors 106, 108 are connected by the low noise cables 110, 112 to the electronic controller 114 at ports 140 and 142, and the stepper motors 120, 124 are connected to the controller 114 by cable 126 at port 148. The controller 114 contains all of the scanning electronics necessary for supplying detector bias voltages, processing the detector outputs, establishing gains, detecting peak output levels, and providing electrical excitation to the stepper motors 120, 124. A cable 115 (FIG. 1) connects the controller 114 to the serial port of the computer 116. The controller 114 sends measurement data to the computer 116 and receives commands from the computer for initial setup and stepper motor control. The stepping motors 120, 124, as well as many of the functions of the controller, are controlled by software residing within the computer 116.

Once the phantom tank 104 has been positioned and filled, the scanning bars 130, 132 properly aligned, and the necessary electronic connections made, the complete operation of the system is controlled by the appropriate software/program residing in the computer 116 located at the accelerator console area (not shown). The operator need only use a computer mouse or pointing device to activate screen commands and operate (by hand) the appropriate controls on the accelerator console. A Windows™ type, user interface environment provides on screen control of all segments of the program. As FIG. 1 illustrates, a printer 118 is provided for generating a hard copy of the measurement data. A printout of the data can be accomplished either at the time of data collection or after the scanning session is completed. The collected data is automatically stored on the computer's hard disk and can be copied to portable media, such as a floppy disk, if an archive copy is desired or if transfer of the data to a treatment planning system is needed.

Figure 3:
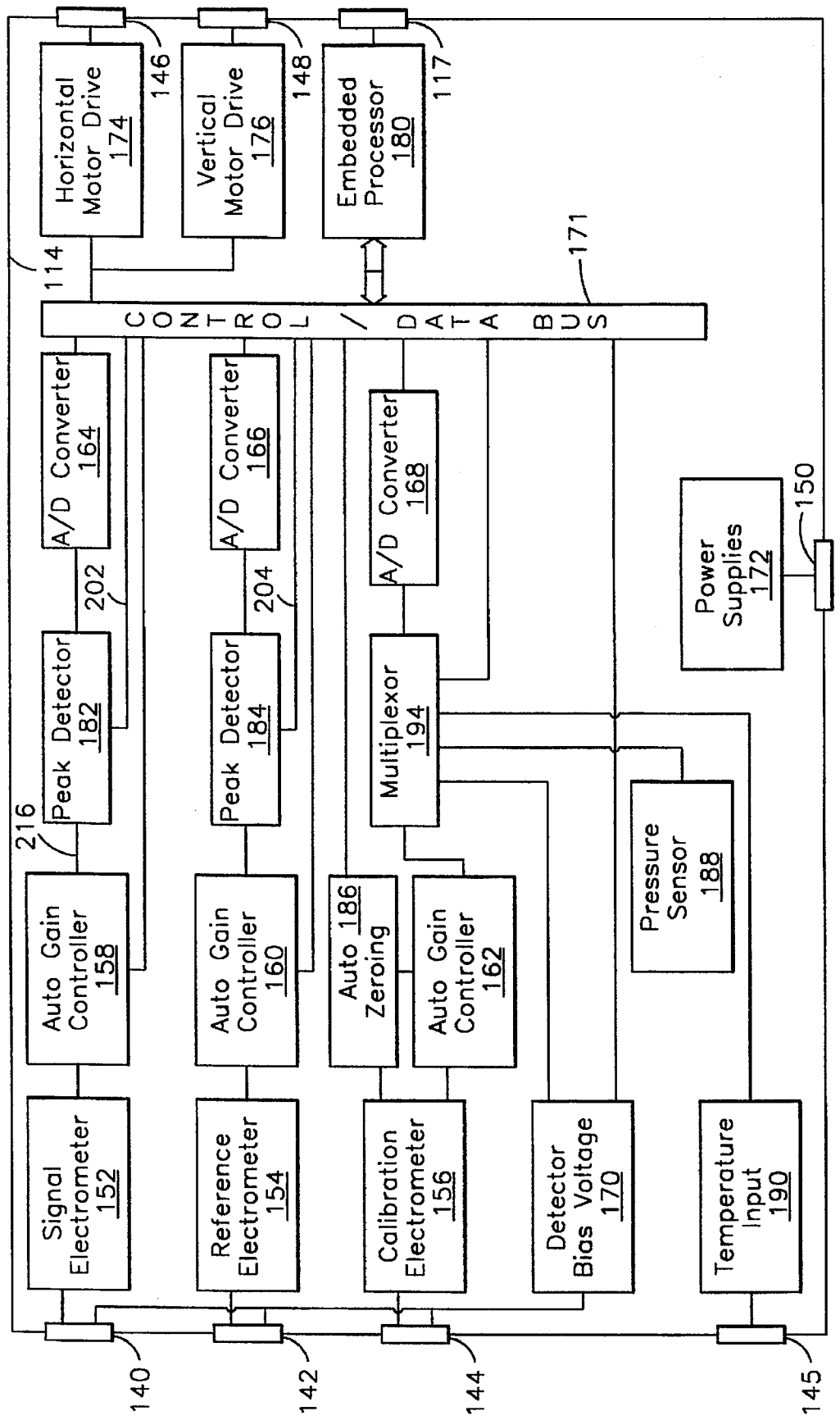
FIG. 3 is a functional block diagram of the controller illustrating internal electronics and external connection ports.

FIG. 3 illustrates a functional block diagram of the controller 114 which includes signal, reference, and calibration electrometers (current-to-voltage converters) 152, 154, 156, auto gain controllers 158, 160, 162, analog-to-digital converters 164, 166, 168, peak detector circuits 182, 184, stepper motor drives 174, 176, detector bias voltage supply 170, pressure sensor 188, temperature input circuit 190, various power supplies 172, and an embedded microprocessor 180. The controller 114 receives the signal detector output at port 140, and the reference detector output is received at port 142. Port 144, which is not used when normal scanning measurements are being taken, is provided for purposes of calibrating the linear accelerator 102, as will be more fully discussed herein. Each of the detector ports 140–144 are supplied with a bias voltage from the detector bias voltage supply 170. For ion chamber detectors, typical bias voltages include ±150 and ±300 Volts, depending on the application. Other external connections to the controller 114 include a temperature sensor connection 145, AC power input 150, stepper motor cable connection 148, and a serial data port 117 for connecting to the computer 116.

The output 110 of the signal detector 106 is received by a signal electrometer 152 which converts the output from a current to a corresponding voltage. Likewise, reference electrometer 154 receives and converts the reference detector output 112 to a voltage. These electrometers 152, 154, or current-to-voltage operational amplifiers, are capable of converting very low current level signals to voltages with a high degree of sensitivity and accuracy. Signal and reference electrometer outputs are received by automatic gain controllers 158, 160 which amplify the electrometer outputs. The outputs of automatic gain controllers 158, 160 are received by peak detector circuits 182, 184 which detect the radiation pulse peaks in the signals.

In a preferred embodiment, peak detection is accomplished by comparing the reference channel analog voltage signal from auto gain controller 160 to a predetermined threshold amplitude. If the voltage signal is greater than or equal to the predetermined threshold, the peak detector circuit 182 begins monitoring the voltage signal for an impending radiation pulse peak. After the peak is detected and the voltage signal drops below the threshold, the peak detector circuit 182 waits for the next peak. In a preferred embodiment, peaks are averaged over a predetermined travel interval of the signal detector 106.

The predetermined threshold is determined prior to scanning by measuring the amplitudes of the radiation pulses being output by the linear accelerator 102 with the reference detector 108. A percent of the peak amplitude as measured by the reference detector 108, such as 50%, is then used to provide a threshold amplitude that determines when peak monitoring will commence and end. With a 50% threshold, peak monitoring begins when the pulse amplitude equals or exceeds 50% of the pulse height and ends at the 50% point of peak drop-off. The peak amplitude value is then digitized by analog-to-digital converters 164, 166 and provided to the control/data bus 171, which is capable of carrying both digital and analog signals. In an alternate embodiment, peak detection is accomplished by monitoring the voltage signal for a predetermined period of time and detecting the peak amplitude value occurring during the predetermined period.

Figure 4:
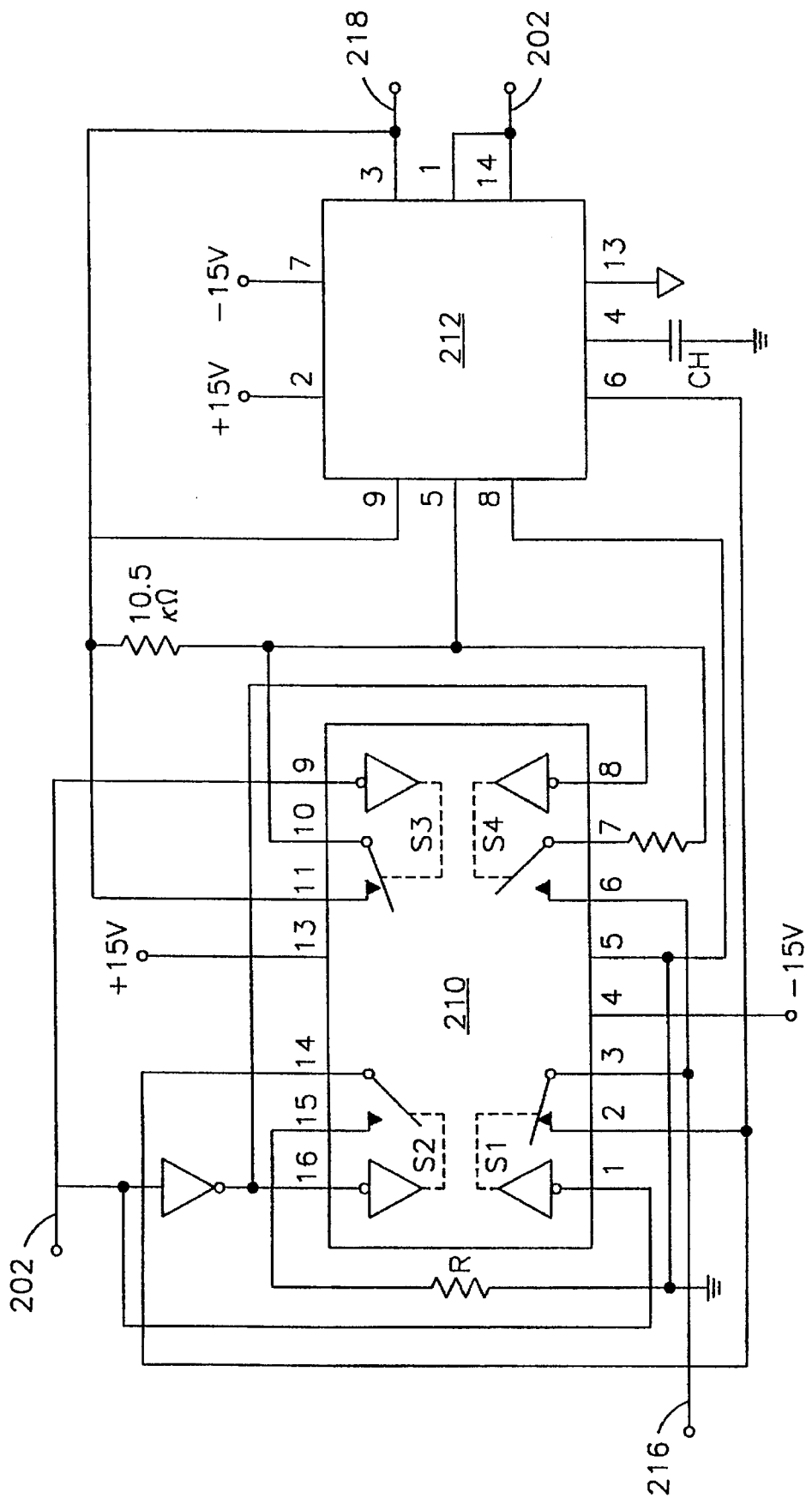
FIG. 4 is a schematic circuit diagram of a peak detector circuit.

FIG. 4 is a schematic circuit diagram illustrating a preferred embodiment of a peak detector circuit. As an exemplary illustration of either of the peak detector circuits 182, 184, FIG. 4 represents a schematic of peak detector circuit 182. The circuit includes a switch 210 and a peak detector chip 212. In a preferred embodiment, switch 210 is an Analog Devices SW202 analog switch, and peak detector chip 212 is an Analog Devices PKD01 peak detector. The output of auto gain controller 158 is received by switch 210 on line 216, and a threshold amplitude value is received on line 202. Switch 210 includes a comparator circuit for comparing the threshold 202 to the signal 216. When the signal 216 equals or exceeds the threshold 202, the signal 216 is provided to peak detector 212 which monitors for a peak amplitude value. Peak monitoring continues until the threshold value is reached on the decreasing side of the peak. At the decreasing slope threshold, peak detector 212 outputs the peak voltage that it detected to A/D converter 164 where the peak is digitized and output to the data bus 171. Peak detector 212 is reset by a signal on line 202 and waits for another peak. In an alternate embodiment, peak detection is implemented digitally.

It will be understood that the system 100 is not limited to use only with pulsed linear accelerators. It may also be used with continuous output linear accelerators as well, such as a cobalt machine. In the case of a continuous output machine, there will be one continuous peak that is continuously detected by the detectors 106, 108.

Embedded processor 180 collects the peak amplitude data from the data bus 171 and processes the data before sending it to the computer 116 via serial port 117. A ratiometric technique is employed to eliminate the effects of accelerometer anomalies and to provide a measure of stability to the data in the event the system experiences such an anomalous event. The signal channel data is divided by the reference channel data and the resultant ratio is provided to the computer 116 and used to indicate the intensity of radiation that was measured at a particular point in the tank 104. Since the data is time tagged along with information representing the position of the signal detector 106 at the time the data was obtained, a map, or distribution of the radiation intensities that were measured can be produced by the computer 116. Preferably, data and position information is stored and correlated to each 0.25 mm movement of the signal detector 106. Programming within the embedded processor 180, which in a preferred embodiment is a 386 microprocessor, also provides a number of control functions within the controller 114, including providing the threshold amplitude value previously discussed to the peak detector circuits 182, 184 via lines 202, 204 respectively. Another function of the embedded processor 180 is to handle all I/O requirements with the computer 116.

Movement of the signal detector 106 through the water 101, as previously described, is controlled by the embedded processor 180. The processor 180 can therefore time tag data and position information for correlation by the computer 116. Programming within the processor 180 calculates each step movement of the stepper motors 120, 124 and sends appropriate commands to the motor drive circuits 174, 176. For example, to move stepper motor 124 one step, a command is generated by the processor 180 and sent to the horizontal motor drive 174 where the command is converted to an amount of electrical excitation which, when received by the stepper motor 124, will drive the motor 124 one step. Likewise, stepper motor 120 is driven by vertical motor drive 176 in response to commands received from the processor 180.

All linear accelerators used for the treatment of malignant neoplasms must be calibrated. To calibrate the linear accelerator 102, the controller 114 includes a calibration electrometer 156. The calibration electrometer 156 receives the electrical current output by one of the detectors 106, 108 and stores the current as electrical charge in a precision capacitor. The amount of charge held by the capacitor is then output by the calibration electrometer 156 in coulomb measurement units.

To calibrate the linear accelerator 102, a determination is made of how much radiation, in units of centigreys, is produced for each monitor unit displayed on the machine console. In other words, calibration of the linear accelerator 102 is performed by determining the adjustment value necessary to establish the accelerator's output at monitor unit for each centigrey of radiation produced. The adjustment value accounts for the difference between the coulomb reading obtained and desired prior to adjustment. The linear accelerator 102 is then calibrated in accordance with the calibration factors so that the linear accelerator 102 outputs one centigrey of radiation per monitor unit. A flow diagram illustrating a preferred method of performing a calibration or a scanning measurement is provided in FIGS. 6A and 6B.

Although the signal detector 106 is preferred since it is moveable, either of the detectors 106, 108 (FIG. 1) may be used for the calibration by connecting the detector's tri-axial cable 110, 112 to the calibration port 144 of the controller 114. For example, the signal detector 106 may be used for performing calibrations by simply disconnecting its cable 110 from port 140 and reconnecting to port 144. In this example, the calibration electrometer 156 receives the output from the signal detector 106 and converts the electrical current generated by the detector 106 to a corresponding voltage signal. The calibration electrometer 156 is under computer control and only requires that the operator turn on the accelerator for the prescribed number of monitor units at the selected energy.

Calibration electrometer 156 is itself calibrated using NIST traceable test equipment to determine the accuracy of the coulomb reading on the computer screen. Since most accelerator calibrations are performed with an ion chamber detector that communicates with the atmosphere, a measurement of the ambient temperature and atmospheric pressure is necessary. An NIST traceable pressure sensor 188 and a temperature sensor 123 are used for this purpose.

The output signal of the calibration electrometer 156 is received and amplified as needed by auto gain controller 162. The amplified and corrected signal produced by the auto gain controller 162 is received by multiplexer 194 where it is multiplexed, along with the outputs from the detector bias voltage 170, pressure sensor 188, and temperature input circuit 190 information, and selectively provided to A/D converter 168 for digitization and output to the data bus 171. From the data bus 171, the embedded processor 180 receives the digitized calibration data, pressure data, temperature data, and bias voltage and provides that information to the computer 116 which calculates the appropriate coulomb readings.

Software residing in the computer 116 provides the data and procedures to comply with the AAPM Task Group 21 (Photon) and Task Group 25 (Electron) protocols. To comply with these protocols, the calibration electrometer 156 differs from the scanning electrometers in that it provides an output in coulombs (C). Detector calibrations are reported in units of Greys per coulomb, so the calibration measurement is made in compatible units. The calibration electrometer 156 is an integrating, self-zeroing electrometer. After the charge on the detector has been measured, an auto zeroing circuit 186 automatically senses that the charge has been read and then discharges the detector. An archive of the calibration data is maintained for periodic review, trend analysis, and comparison with future calibrations.

Figure 5A:
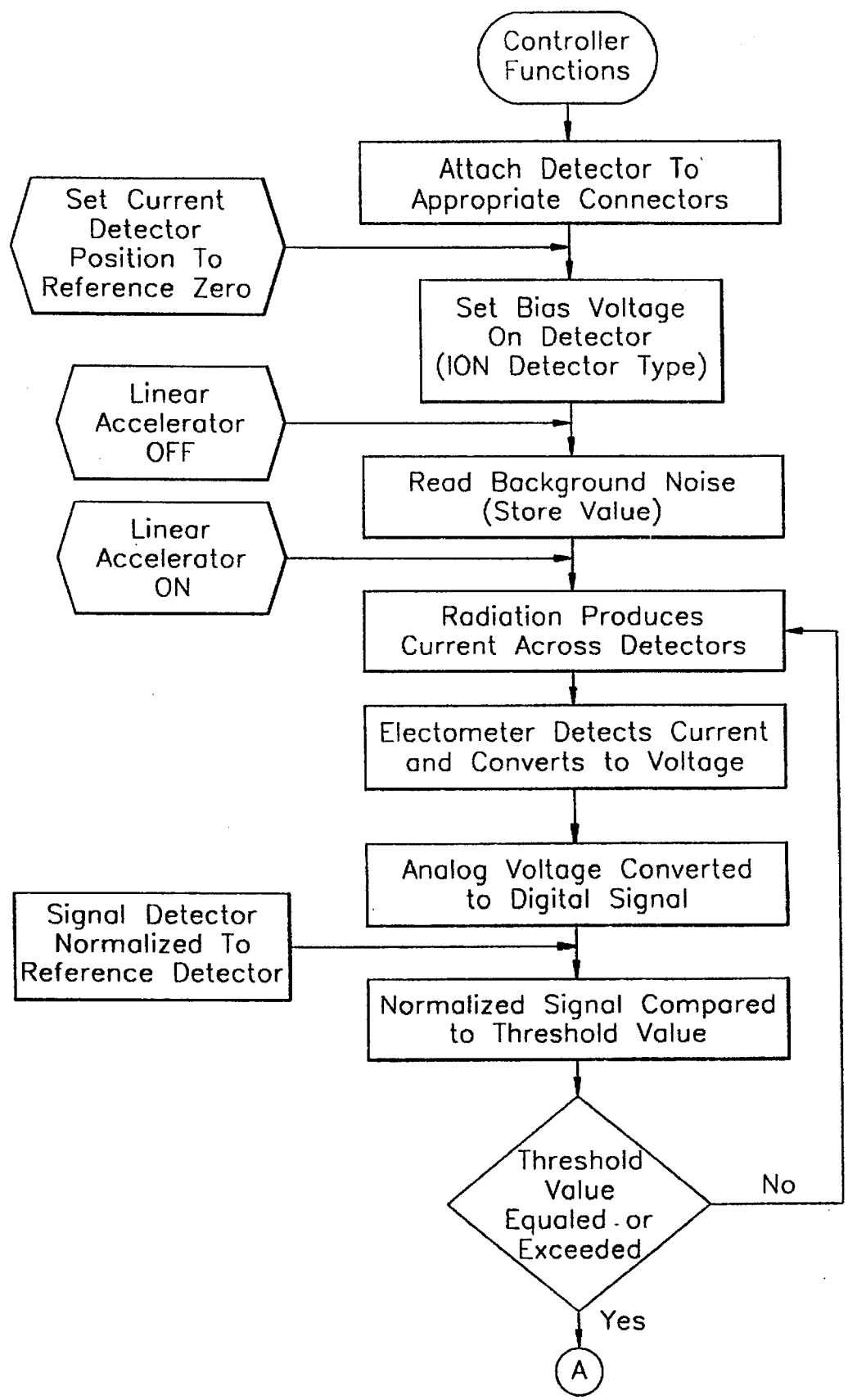
FIGS. 5A and 5B collectively are a flow diagram illustrating the sequential operation of the controller for conducting scanning measurements.
Figure 5B:
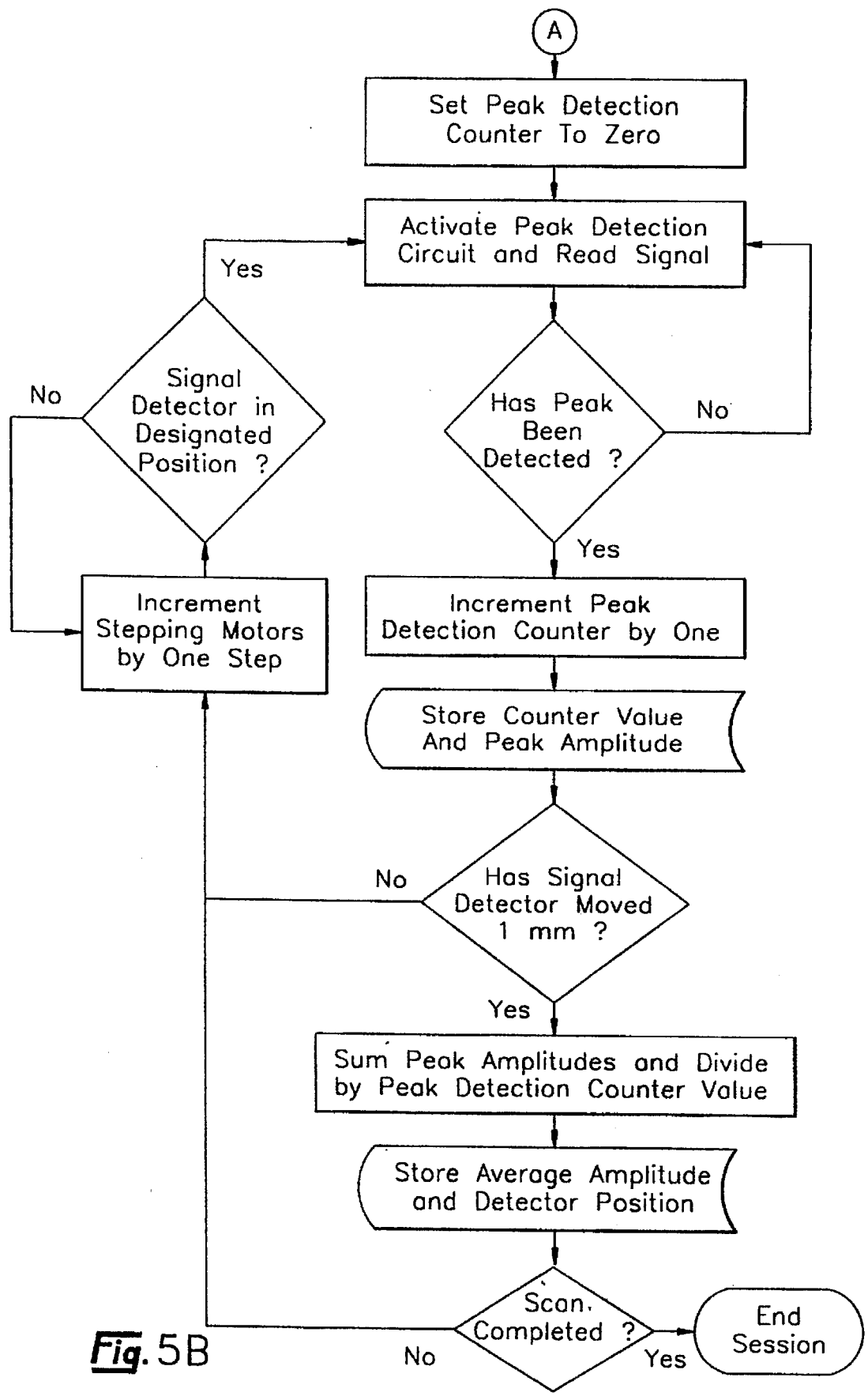

The flow diagram of FIGS. 5A and 5B illustrates the sequential operation of the controller 114 for performing scanning measurements. The functions of the controller 114 are regulated by software residing in the embedded processor 180 and computer 116. After the appropriate system setup connections are made, the position of the signal detector 106 is set to zero reference and a bias voltage is applied to each of the detectors 106, 108.

With continued reference to FIGS. 5A and 5B, the controller 114 continues to monitor for, and store the amplitude values of, radiation pulse peaks until the signal detector 106 has moved a predetermined distance, such as 1 mm. When the signal detector 106 has moved 1 mm, each of the peak amplitude values that were detected and stored during the 1 mm of movement are summed and divided by the value of the peak detection counter to produce an average peak amplitude value over the 1 mm. The average value is stored along with the signal detector position, and the process is repeated until the desired scan pattern (i.e., profiles, isodose lines, depth dose curves, etc.) is completed.

In a preferred embodiment, movement of the signal detector 106 through the phantom tank 104 is automatically set at an optimal speed based on the pulse rate of the accelerator 102. Prior to initiating a measurement scan, the system 100 will read the pulses being emitted by the accelerator 102 for a period of time with one of the detectors 106, 108 to ascertain the pulse rate of the accelerator 102. The speed of the signal detector 106 is then set so as to capture a predetermined number of pulses during each 1 mm of detector 106 movement. Preferably, the speed of the signal detector 106 is such that at least one radiation pulse will be output by the linear accelerator 102 for each 0.25 mm of detector movement for a total of at least four pulses that will be averaged over each 1 mm of detector travel.

The peak detector circuit 182 and stepper motors 120, 124 are fast enough to outpace the pulse generation of the accelerator 102, thus ensuring that all pulses generated will be captured with the signal detector 106 in proper position. Some accelerators 102 maintain their output by occasionally dropping pulses. This presents a problem for systems that integrate over a period of time, but presents no difficulty for a peak detection system since the system will simply average fewer pulses.

It will be appreciated that peak detection allows the signal detector 106 to be moved continuously and therefore detect the pertinent data much more rapidly. For example, a depth dose scan from the surface of the water to a depth of 35 cm requires about 10 seconds at a movement rate of 3.5 cm per second. Since the present system 100 employs a variable speed rate capability (2 cm to 5 cm per second), the depth dose scan could conceivably be accomplished in as little as 7 seconds. A more dramatic reduction in time is noticed when performing beam profiles at a number of depths.

The percent depth dose (PDD) is the ratio of the radiation intensity at any point along the central axis to the intensity at the point of maximum dose ($D_{max}$). Therefore, the PDD is 100% at $D_{max}$ and some lesser value at all other points. The PDD at a depth of 10 cm is considered to be a representation of the energy of the radiation beam 134. Evaluation of the accuracy of the PDD measured by the scanner system 100 is accomplished by comparison with static, non-moving measurements at selected points along the central axis and determining the percent difference. When performing this function for electrons, the measurement term is percent depth ionization (PDI). In order to comply with the AAPM TG-25 protocol, the bias voltage polarity is automatically reversed by the embedded processor 180 at the maximum depth of the scan, and data is collected during ascent of the signal detector 106 with this reversed bias voltage. The two scans (descent and ascent) are then averaged for the PDI data. Scanned values that are within 1% of the static measurements are considered acceptable. Several energies from several different accelerators were evaluated with the present system, and all measurements were within the 1% requirement.

Since actual amplitude values from the pulse train generated by the accelerator 102 are used, the system 100 has the stability of the accelerator energy output. This is usually specified at the 2% level, but once an accelerator 102 is installed and properly tuned energy bandwidths of less than 1% are common. As a result, the system 100 requires no mathematical smoothing techniques. Indeed, the data generated by the system 100 can be used as an indicator of the energy stability of the accelerator 102. The system 100 takes advantage of this high level of stability by incorporating a calibration mode, as previously discussed.

Figure 6A:
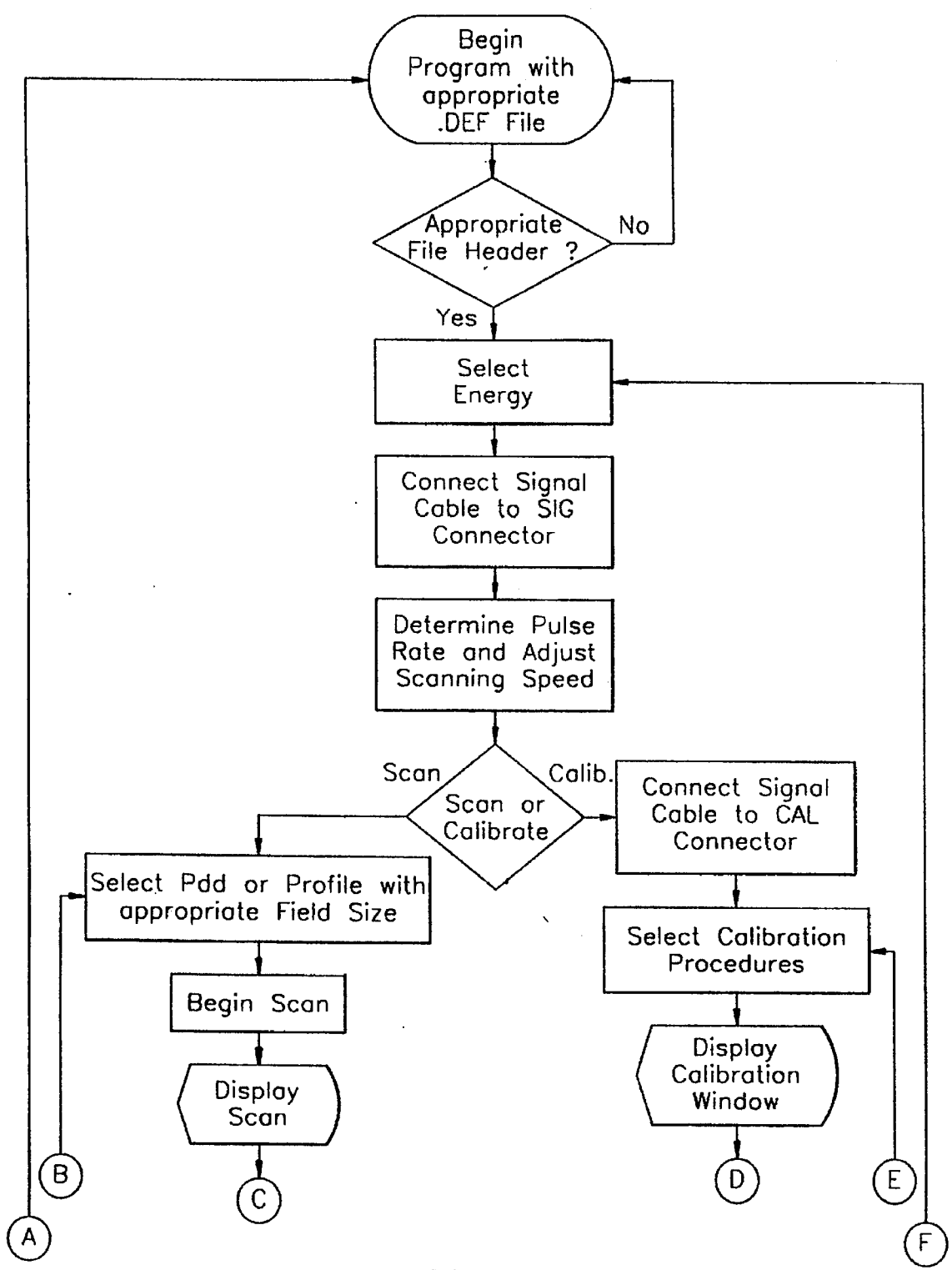
FIGS. 6A–C collectively are a flow diagram illustrating system level steps for performing scanning measurements or calibrations.
Figure 6B:
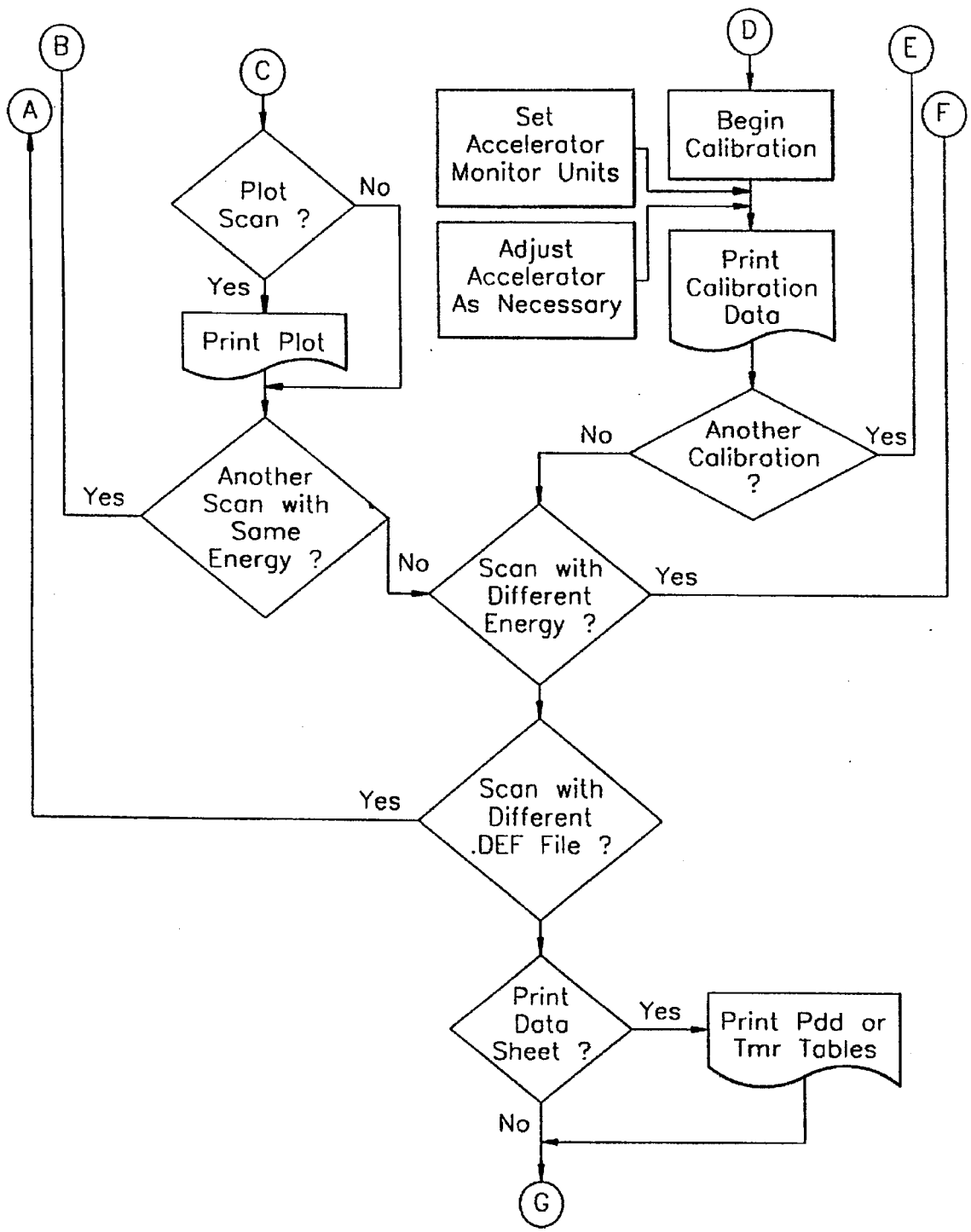
Figure 6C:
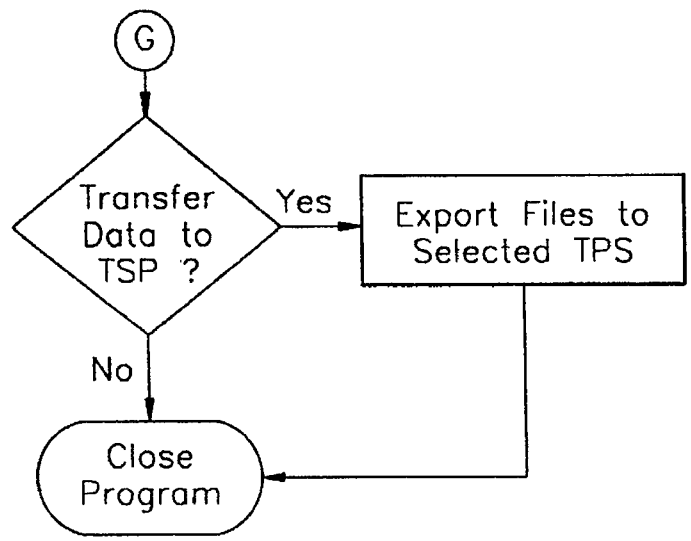
Figure 7A:
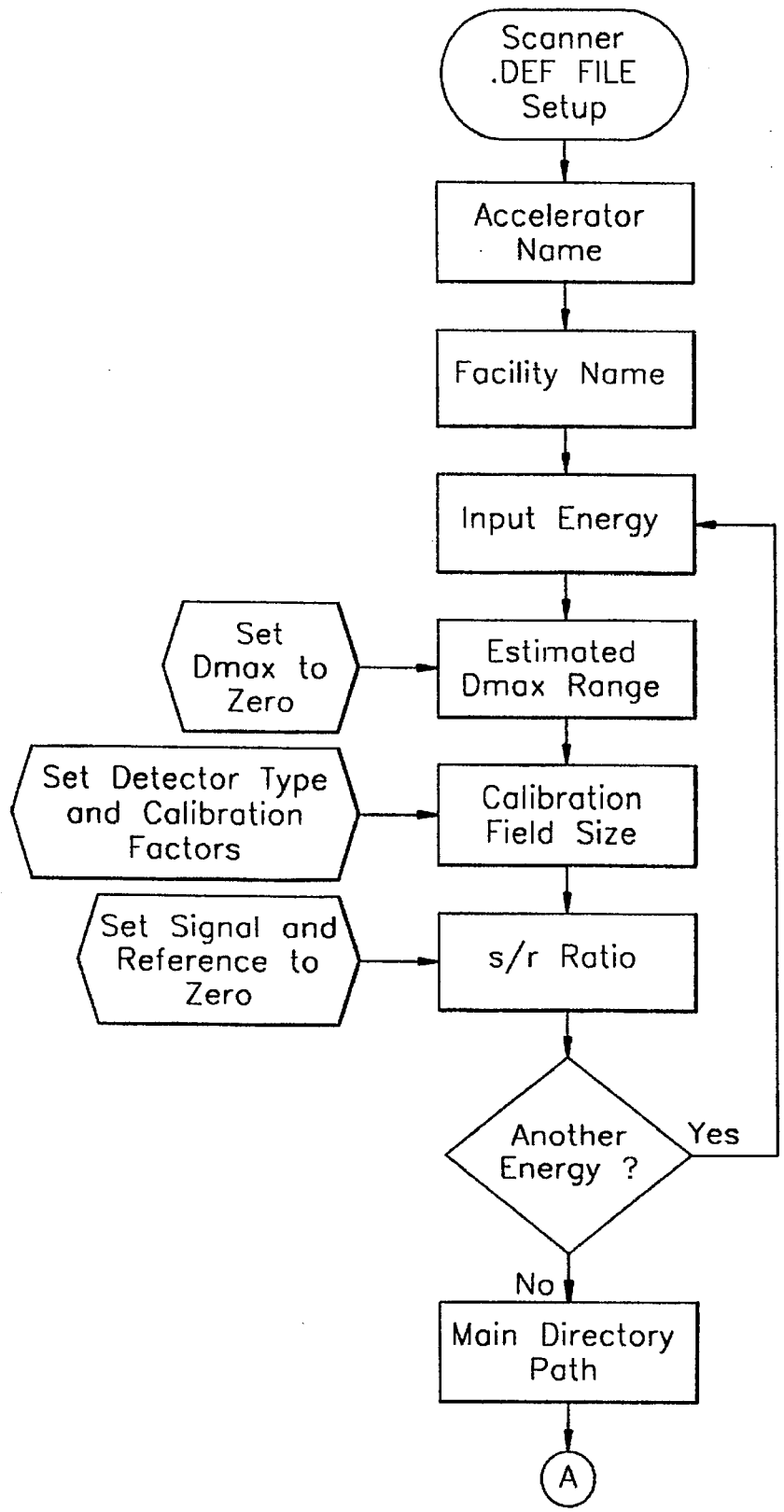
FIGS. 7A–C collectively are a flow diagram illustrating the steps for creating a definition (.DEF) file for scanning.
Figure 7B:
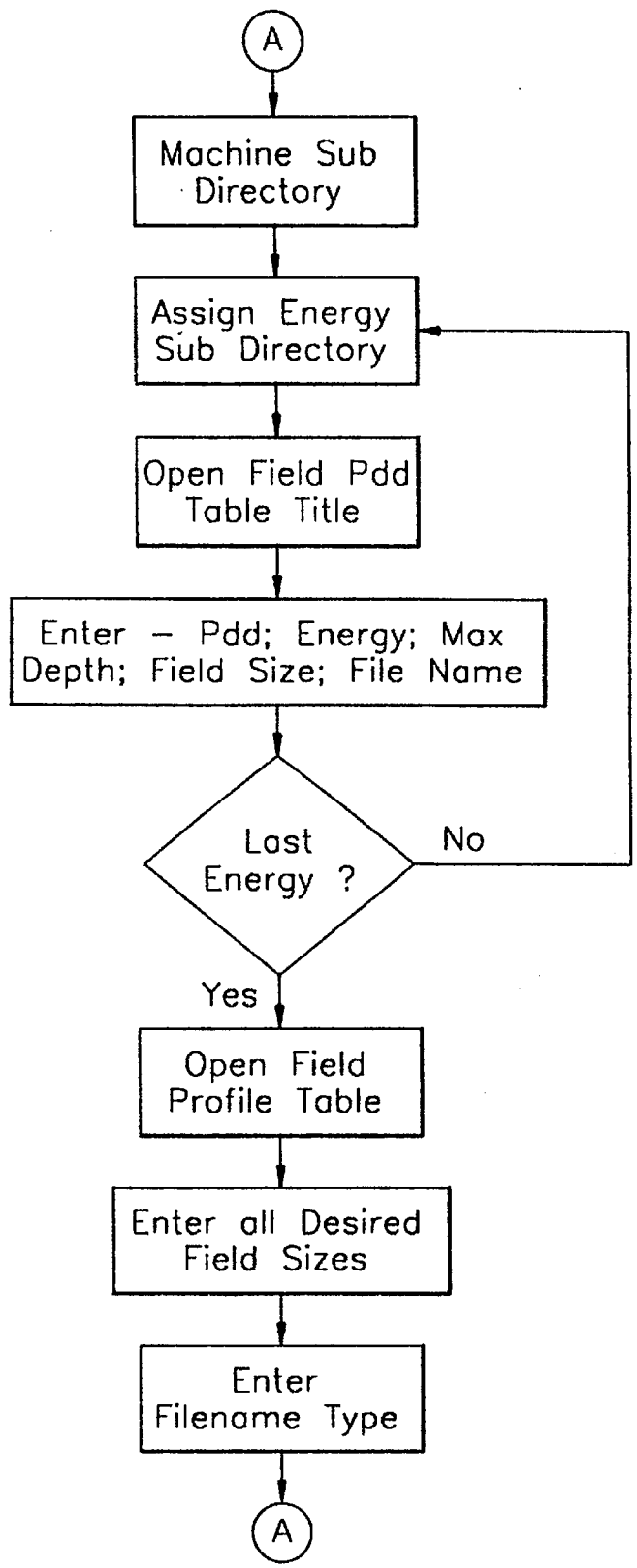
Figure 7C:
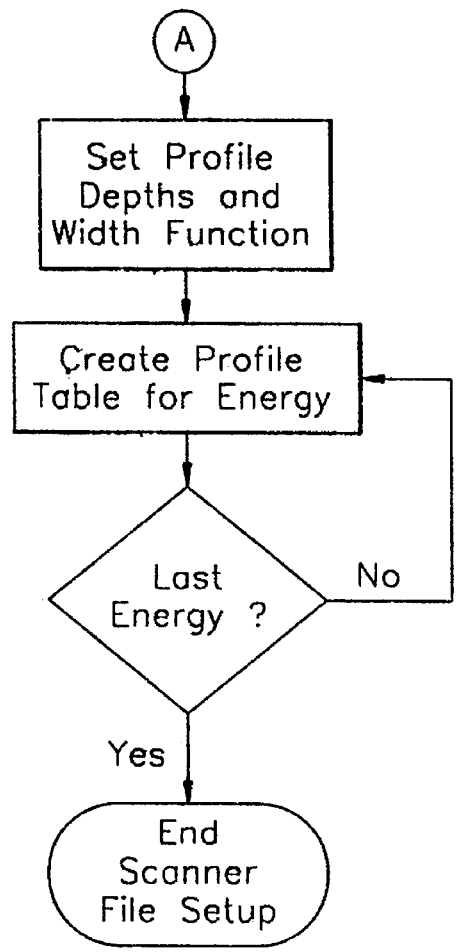

As illustrated by the flow diagram of FIGS. 6A and 6B, scanning measurements, as well as calibrations, are performed in accordance with a .DEF file (definition file). FIGS. 7A and 7B provide a flow diagram illustrating the steps involved in setting up a .DEF file. In a preferred embodiment, .DEF files are set up with the use of computer 116. A single WINDOWS™ type, user interface screen controls all segments of the program. The .DEF file defines, in addition to basic information such as the facility name, each of the scanning or calibration parameters that may be used at some point during the scanning or calibration session. Parameters such as $D_{max}$, calibration factors, directory path and filename where data will be automatically stored on the computer's hard disk, and energy level profiles are defined and stored in the .DEF file. After completion of the scan or calibration in accordance with the .DEF file, the data may be printed on an attached printer 118 (FIG. 1) and/or transferred to a treatment planning system (TPS) if needed. The print out of the data can be accomplished either at the time of data collection or after the scanning or calibration session is completed.

It is contemplated, and will be apparent to those skilled in the art from the foregoing specification and drawings that modifications and/or changes may be made in the embodiments of the invention. Accordingly, it is expressly intended that the foregoing are illustrative of preferred embodiments only, not limiting thereto, and that the true spirit and scope of the present invention be determined by reference to the appended claims.

What is claimed is:

1. A method of calibrating a medical linear accelerator comprising the steps of:

providing a medium for receiving radiation from the linear accelerator;

sensing radiation produced by the linear accelerator with a radiation detector disposed within the medium, said radiation detector producing a detector output in the form of an electrical current representative of the amount of radiation output by the linear accelerator;

providing an integrating, automatic, self-zeroing, calibration electrometer for converting the detector output from an electrical current to an electrical voltage corresponding to the amount of radiation output by the linear accelerator; and determining from said electrical voltage an adjustment value necessary to bring the linear accelerator into calibration.

2. The method of claim 1 wherein said adjustment value is determined as the difference between the amount of output radiation indicated by said electrical voltage and the amount of radiation desired to be output by the linear accelerator per monitor unit.

3. The method of claim 2 wherein the amount of radiation desired to be output by the linear accelerator per monitor unit is determined in accordance with an established protocol.

4. The method of claim 3 wherein said established protocol is one monitor unit per centigrey of radiation.

5. The method of claim 1, further comprising the step of adjusting the linear accelerator output in accordance with the adjustment value.

6. A method of calibrating a medical linear accelerator comprising the steps of:

providing a medium for receiving radiation from the linear accelerator;

sensing radiation produced by the linear accelerator with a radiation detector, producing a detector output in the form of an electrical current representative of the amount of radiation output by the linear accelerator;

providing a computer-controlled, integrating, self-zeroing electrometer for converting the detector output from an electrical current to an electrical voltage corresponding to the amount of radiation output by the linear accelerator; and determining from said electrical voltage an adjustment value necessary to calibrate the linear accelerator so that one monitor unit represents one centigrey of radiation.

7. A method of calibrating a medical linear accelerator comprising the steps of:

providing a medium for receiving radiation from the linear accelerator;

sensing radiation produced by the linear accelerator with a radiation detector, producing a detector output in the form of an electrical current representative of the amount of radiation output by the linear accelerator;

providing a computer-controlled, integrating, self-zeroing electrometer for converting the detector output from an electrical current to an electrical voltage corresponding to the amount of radiation output by the linear accelerator;

determining the difference between the amount of radiation output represented by said electrical voltage and the amount of radiation output desired; and adjusting the linear accelerator in accordance with said difference.

* * * * *